(12) United States Patent
Sekimoto (10) Patent No.: US 8,325,329 B2
(45) Date of Patent: Dec. 4, 2012

(54) SAMPLE DETECTOR AND MEASUREMENT DEVICE EQUIPPED WITH THE SAME

(75) Inventor: Shinjiro Sekimoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 393 days.

(21) Appl. No.: 12/734,254

(22) PCT Filed: Oct. 25, 2008

(86) PCT No.: PCT/JP2008/069380
§ 371 (c)(1),
(2), (4) Date: Apr. 21, 2010

(87) PCT Pub. No.: WO2009/054516
PCT Pub. Date: Apr. 30, 2009

(65) Prior Publication Data
US 2010/0259747 A1  Oct. 14, 2010

(30) Foreign Application Priority Data
Oct. 26, 2007  (JP) .................................. 2007-278829

(51) Int. Cl.
*G01N 33/48* (2006.01)
(52) U.S. Cl. ........................................................ 356/39
(58) Field of Classification Search .................... 356/39, 356/40, 432, 434
See application file for complete search history.

(56) References Cited

U.S. PATENT DOCUMENTS

| | | | |
|---|---|---|---|
| 4,160,646 A * | 7/1979 | Furutani et al. | 436/169 |
| 5,597,532 A * | 1/1997 | Connolly | 422/401 |
| 5,889,585 A | 3/1999 | Markart | |
| 6,055,060 A * | 4/2000 | Bolduan et al. | 356/433 |
| 6,707,554 B1 * | 3/2004 | Miltner et al. | 356/433 |
| 7,477,404 B2 * | 1/2009 | Schulat et al. | 356/614 |
| 2006/0240541 A1 | 10/2006 | Petruno et al. | |

FOREIGN PATENT DOCUMENTS

| | | |
|---|---|---|
| JP | 02-003467 A | 1/1990 |
| JP | 08-020364 A | 1/1996 |
| JP | 2000-263398 A | 9/2000 |

(Continued)

OTHER PUBLICATIONS

International Search Report mailed on Dec. 16, 2008.

*Primary Examiner* — Roy M Punnoose
(74) *Attorney, Agent, or Firm* — Rader, Fishman & Grauer PLLC (57) ABSTRACT

A sample detector B includes a member 6 provided with an aperture 60, as well as a light receiving element 5 which receives two light beams directed from a pair of light sources 40, 41 to a detection area AR and having passed through the detection area and outputs a signal corresponding to the amount of light received, and a determination means 8 for determining whether or not a sample is properly supplied to the detection area AR based on the signal. Two light beams emitted from the paired light sources 40, 41 travel through paths defined by the aperture 60 to regions ARr, ARf of the detection area AR which are positionally deviated from each other. With this arrangement, whether or not a sample is properly supplied to the detection area AR is precisely determined without using an expensive component such as an optical lens.

11 Claims, 7 Drawing Sheets

FOREIGN PATENT DOCUMENTS

| | | |
|---|---|---|
| JP | 2002-525625 A | 8/2002 |
| JP | 3455654 B2 | 7/2003 |
| JP | 2004-163393 A | 6/2004 |
| JP | 2004-163411 A | 6/2004 |
| JP | 2006-162496 A | 6/2006 |
| JP | 2006-208386 A | 8/2006 |
| WO | WO 00/19185 | 4/2000 |
| WO | WO 2007/007849 A1 | 1/2007 |

\* cited by examiner

SAMPLE DETECTOR AND MEASUREMENT DEVICE EQUIPPED WITH THE SAME

TECHNICAL FIELD

The present invention relates to a sample detector for determining whether or not a sample such as blood is properly supplied to a predetermined area. The invention also relates to a measurement device provided with such a sample detector.

BACKGROUND ART

Examples of conventional sample detector are disclosed in Patent Documents 1-3 identified below. In the sample detectors disclosed in these documents, a predetermined detection area is irradiated with light from a light source, and light reflected by or transmitted through the detection area is received by a light receiving element. Based on the reflectivity or transmittance of the detection area, whether or not a sample is present in the detection area is determined. In Patent Documents 2 and 3, a pair of light sources are used to irradiate two separate regions with light. With this arrangement, it is possible to determine whether or not a sufficient amount of sample is present over two regions, so that the detector is applicable to a relatively large detection area.

In the sample detector, if light is simply directed toward the detection area, the light reaches also the portions other than the detection area, whereby light passing through the portions other than the detection area may be received by the light receiving element. In this case, erroneous determination may be made as to whether or not a sample is properly present in the detection area. Therefore, the sample detectors disclosed in Patent Documents 1-3 employ or require a means to guide the light emitted from the light source properly to the detection area by using an optical lens.

However, the use of an optical lens as described above increases the component cost. Further, the incorporation of an optical lens in a device complicates the structure of the device and hence increases the manufacturing cost of the device. Moreover, since a space for placing the optical lens is necessary, the overall device becomes large. These problems are more serious in the case where the device includes a plurality of light sources, because a plurality of optical lenses are necessary.

Patent Document 1: JP-A-2004-163393
Patent Document 2: Japanese Patent No. 3455654
Patent Document 3: U.S. Pat. No. 5,889,585

DISCLOSURE OF THE INVENTION

Problems to be Solved by the Invention

An object of the present invention is to provide a sample detector which is capable of solving or alleviating the above-described problems and a measurement device provided with such a sample detector.

Means for Solving the Problems

To solve the above-described problems, the present invention takes the following technical measures.

According to a first aspect of the present invention, there is provided a sample detector including at least a pair of light sources for irradiating a detection area as a destination of sample supply with light, and a light receiving element which receives two light beams directed from the paired light sources to the detection area and having passed through the detection area and outputs a signal corresponding to the amount of light received. The sample detector further includes a member provided with at least one aperture positioned between the paired light sources and the detection area. The two light beams emitted from the paired light sources travel through paths defined by the aperture to regions in the detection area which are positionally deviated from each other.

Preferably, the aperture is positioned between the paired light sources in a direction in which the paired light sources are aligned so that both of the two light beams emitted from the paired light sources enter the aperture, and the paths of the two light beams are defined by one aperture.

Preferably, the sample detector according to the present invention further includes a determination means. When the paired light sources are individually turned on with a time difference, if levels of two signals outputted from the light receiving element are within a predetermined range and difference between the levels is not more than a predetermined threshold, the determination means determines that a sample is properly supplied to the detection area, and if not so, the determination means determines that a sample is not properly supplied to the detection area.

Preferably, the determination means sets, as a reference signal, a signal outputted from the light receiving element when the paired light sources are individually turned on in a state in which the sample is not supplied to the detection area. In determining whether or not a sample is supplied to the detection area, the determination means corrects a signal outputted from the light receiving element to a signal having a relative value to the reference signal and makes determination based on the corrected signal.

Preferably, in the sample detector according to the present invention, the two light beams emitted from the paired light sources do not overlap each other in the detection area or overlap each other with an overlap width which is smaller than about 4/5 of the width of each of the light beams.

Preferably, light which has entered the aperture while spreading from a light emitting surface of each of the light sources to a width larger than the width of the light emitting surface passes through the aperture to reach the detection area.

Preferably, the two light beams emitted from the paired light sources partially overlap each other on the light receiving element.

Preferably, a member provided with an additional aperture for allowing light having passed through the detection area to travel toward the light receiving member is arranged between the detection area and the light receiving element so that external disturbing light which has not passed through the detection area is prevented from traveling toward the light receiving element.

According to a second aspect of the present invention, there is provided a measurement device including a sample detector which sets a destination of sample supply as a detection area, and a measurement means capable of performing predetermined measurement with respect to a sample supplied to the detection area. The sample detector includes at least a pair of light sources for irradiating the detection area with light, a light receiving element which receives two light beams directed from the paired light sources to the detection area and having passed through the detection area and outputs a signal corresponding to the amount of light received, and a member provided with at least one aperture positioned between the paired light sources and the detection area. The two light beams emitted from the paired light sources travel through paths defined by the aperture to regions of the detection area which are positionally deviated from each other.

Preferably, the measurement means is capable of measuring concentration of a particular component in a blood sample. When a blood sample is caused to flow successively to each of the two positionally deviated regions of the detection area from one side thereof, speed of the flow of the blood sample is determined based on an output signal from the light receiving element which is obtained by directing light from the two light sources to the two regions, and information about hematocrit of the blood sample is obtained.

Preferably, the measurement means includes at least one additional light source. Light emitted from the additional light source is received by the light receiving element after passing through the aperture and traveling to the detection area, and information about concentration of a particular component in the blood sample is obtained based on an output signal from the light receiving element.

Other features and advantages of the present invention will become more apparent from the detailed description of embodiments given below with reference to the accompanying drawings.

BRIEF DESCRIPTION OF THE DRAWINGS

FIG. 2A is a sectional view of a sensor for use with the measurement device illustrated in FIG. 1, whereas

FIG. 7A is a view schematically illustrating a comparative example relative to the embodiment illustrated in FIGS. 1-4, whereas

FIG. 8A is a view schematically illustrating another comparative example relative to the embodiment of the present invention illustrated in FIGS. 1-4, whereas

BEST MODE FOR CARRYING OUT THE INVENTION

Preferred embodiments of the present invention are described below in detail with reference to the accompanying drawings.

Figure 1:
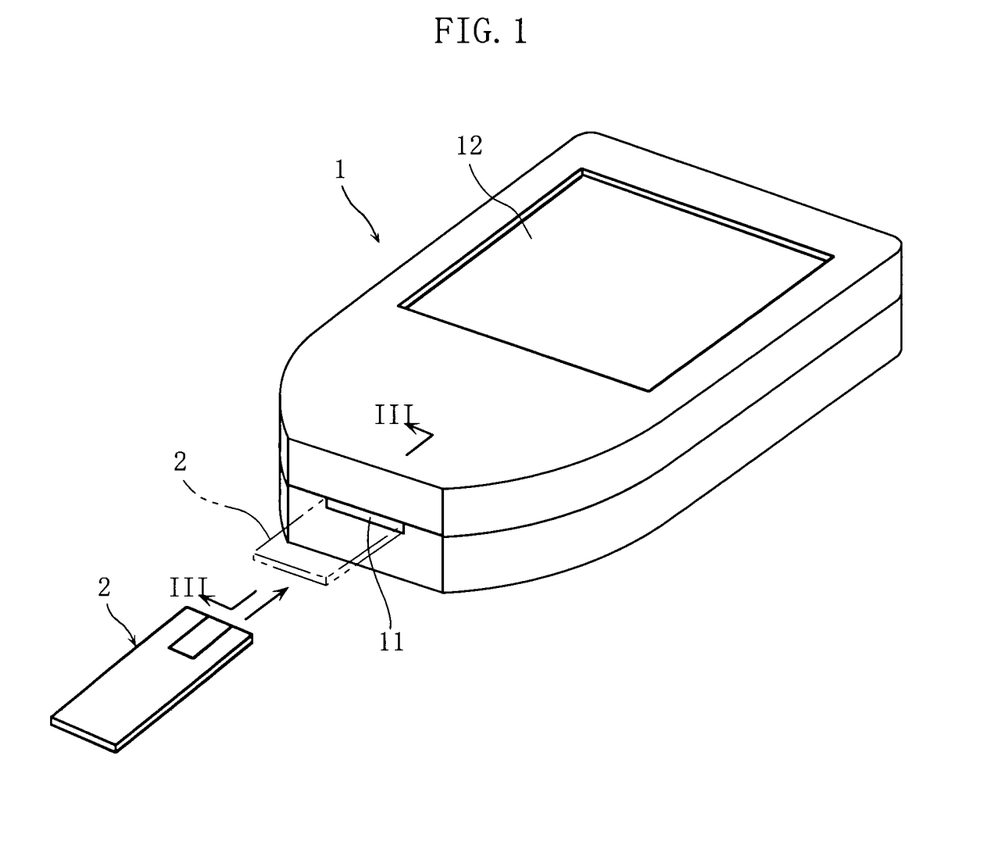
FIG. 1 is an external view illustrating an example of measurement device according to the present invention.

FIGS. 1 to 4 illustrate an example of measurement device provided with a sample detector according to the present invention and its related structure. The measurement device A illustrated in FIG. 1 is a portable blood glucose level measurement device designed to measure the glucose level in blood by an optical technique. The measurement device includes a case 1 provided with a display 12 on the obverse surface. The display 12 is made by using e.g. a liquid crystal panel. As will be described later, a means for measuring the glucose concentration in a blood sample and a sample detector B for determining whether or not a sample is properly supplied to a predetermined detection area are provided in the case 1. The measurement device A uses a blood sampling sensor 2 in measuring the glucose concentration, and the case 1 has an end formed with an opening 11 for inserting the sensor 2.

Figure 2:
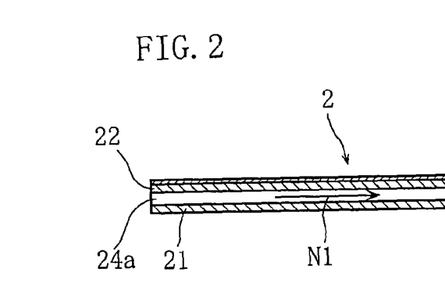
Figure 2A:
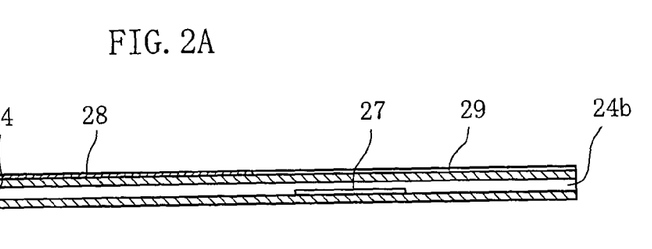
Figure 2B:
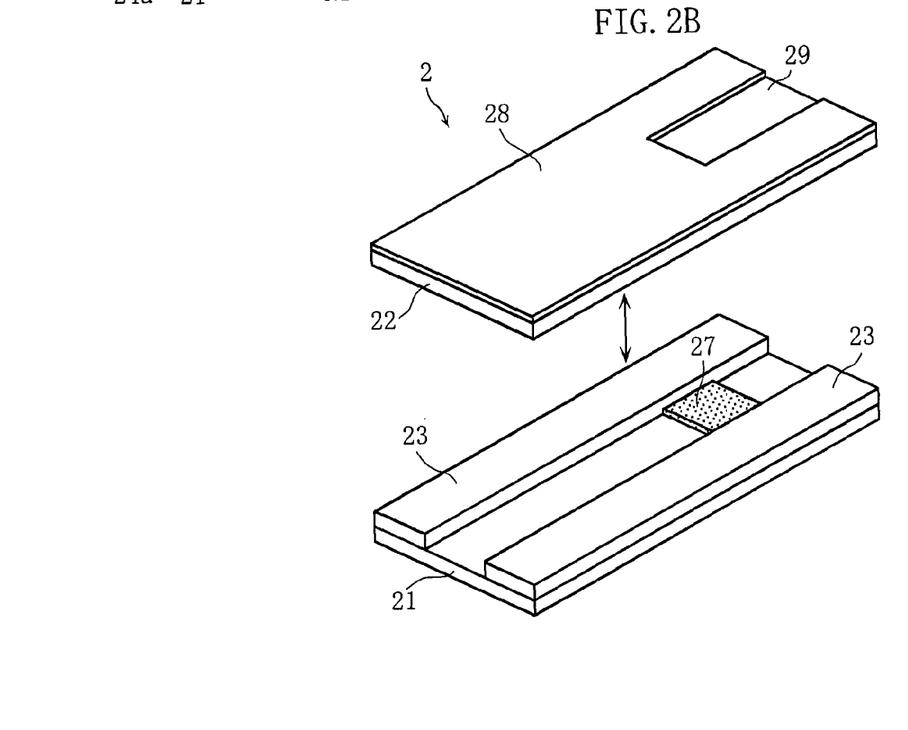
FIG. 2B is an exploded perspective view of the sensor.

As illustrated in FIGS. 2A and 2B, the sensor 2 is in the form of a rectangular strip and made up of a first and a second sheet pieces 21 and 22 bonded together via a pair of spacers 23. The sensor 2 is formed therein with a capillary 24 surrounded by the above-described members 21-23. When blood is applied to an end opening 24a of the capillary 24, the capillary functions to move the blood toward the other end opening 24b by capillary action as indicated by the arrow N1. The movement of the blood stops when part of the blood reaches the end opening 24b.

A reaction portion 27 is provided at a portion of the capillary 24. The reaction portion 27 includes a reagent for reaction with glucose in blood, and a color developing agent. When blood reaches the reaction portion 27, a predetermined liquid phase reaction system is established, so that color development occurs correspondingly to the glucose concentration. Examples of the reagent include glucose dehydrogenase as an oxidoreductase. Examples of the color developing agent includes "WST-4"(2-Benzothiazolyl-3-(4-carboxy-2-methoxyphenyl)-5-[4-(2-sulfoethylcarbamoyl)phenyl]-2H-tetrazolium)) manufactured by DOJINDO LABORATORIES of Japan. The reaction portion 27 may further include a substance (e.g. hexaammineruthenium (III) chloride) which promotes the color developing reaction corresponding to the glucose concentration.

The measurement device A obtains a glucose concentration by applying light to a point of the reaction portion 17 at which the above-described liquid phase reaction system is established and measuring the light absorptance. However, the light absorptance is influenced by the hematocrit of the blood (the ratio of the volume (%) occupied by red blood cells to the volume of the whole blood). Therefore, as will be described later, the measurement device A is designed to obtain information about the hematocrit of the blood and correct the measurement of the glucose concentration based on the information.

The first and the second sheet pieces 21 and 22 of the sensor 2 are made of a resin having a high light transmittance. A light-shielding mask 28 formed with an opening 29 is provided on the upper surface of the second sheet piece 21. The opening 29 is positioned directly above the reaction portion 27, so that light is prevented from impinging on the reaction portion 27 through portions other than the opening 29.

Figure 3:
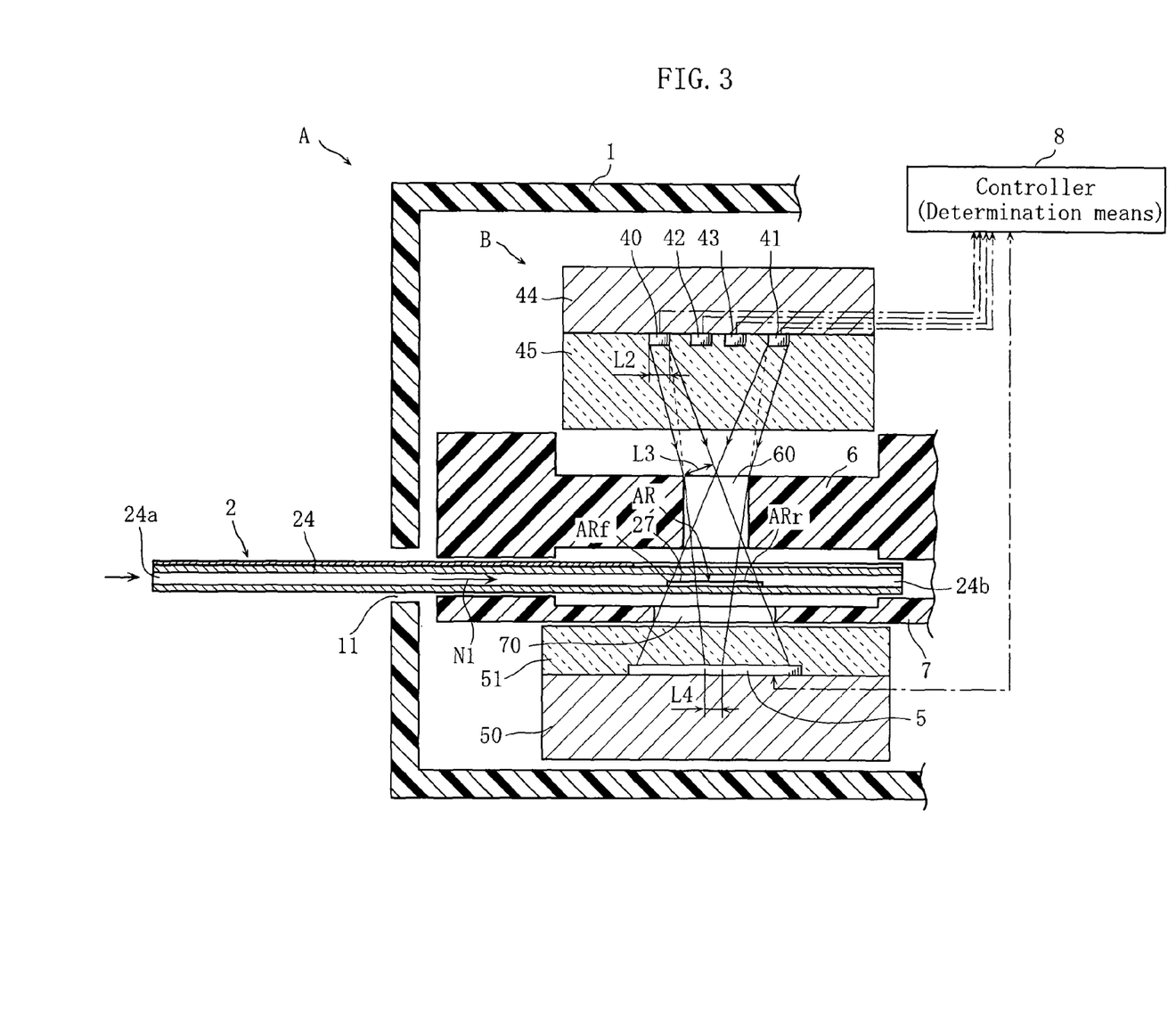
FIG. 3 is a schematic sectional view taken along lines in FIG. 1.

As illustrated in FIG. 3, the sample detector B is provided in the case 1 of the measurement device A. With the sensor 2 inserted into the case 1 through the opening 11 and set at a predetermined position, the sample detector B serves to determine whether or not blood is sufficiently supplied to the reaction region 27 as a detection area AR.

The sample detector B includes a pair of light sources 40 and 41 for blood detection, a pair of light sources (additional light sources) 42 and 43 for measurement of glucose concentration of blood, a light receiving element 5, a first light path defining member 6 formed with an aperture 60, a second light path defining member 7 formed with an aperture 70 (additional aperture) and a controller 8.

The light sources 40-43, which are made of LEDs, are mounted on a suitable substrate 44 and sealed with transparent resin 45. The light sources 40-43 can be individually turned on by the control of the controller 8. The light sources are positioned above the detection area AR and aligned at predetermined intervals in the direction in which blood flows (the direction indicated by the arrow N1). Preferably, the light sources 40 and 41 emit light having a peak wavelength in a range of 500 to 590 nm, for which blood (red blood cells) have a high absorptance. On the other hand, the light sources 42 and 43 respectively emit main light and reference light to measure glucose concentration. The main light is light having a peak wavelength in a range of 600 to 700 nm, for example. The reference light is light having a peak wavelength in a range of 800 to 910 nm, for example.

The light receiving element 5 is made by using e.g. a photodiode. The light receiving element receives the light passing downward through the detection area AR and outputs a signal of a level corresponding to the amount of light received to the controller 8. The light receiving element 5 is mounted on a suitable substrate 50, sealed with transparent resin 51 and positioned directly below the detection area AR.

Figure 4:
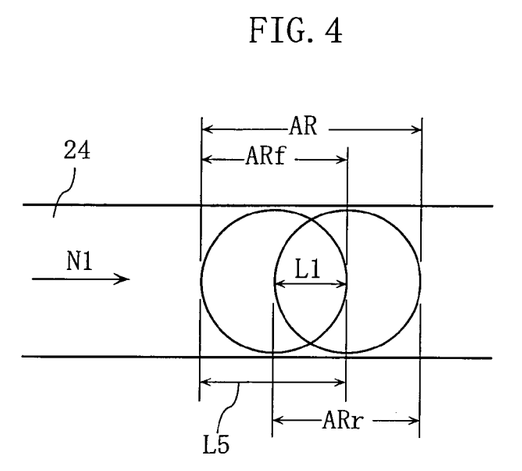
FIG. 4 is an explanatory plan view of a detection area of a sample detector provided in the measurement device illustrated in FIG. 1.

The first light path defining member 6 is made of a material such as a black resin which has a low light reflectance, and positioned above the sensor 2. The aperture 60 of the first light path defining member 6 is positioned between the light sources 40 and 41 in the direction in which the light sources 40 and 41 are aligned (i.e., the blood flow direction indicated by the arrow N1). The aperture 60 functions to adjust the light emitted from the light sources 40 and 41 to guide the light to the detection area AR. As illustrated in FIG. 4, the detection area AR is made up of two generally circular regions positionally deviated from each other in the blood flow direction indicated by the arrow N1, i.e., the region ARf on the upstream side and the region ARr on the downstream side. The light emitted from the light source 40 is adjusted by the aperture 60 to be guided the region ARr on the downstream side. That is, the region ARr is a region to be irradiated with the light from the light source 40. On the other hand, the light emitted from the light source 41 is adjusted by the aperture 60 to be guided to the region ARf on the upstream side. That is, the region ARf is a region to be irradiated with the light from the light source 41.

Preferably, the overlap width L1 of the above-described two regions ARf and ARr (i.e., the overlap width of the light beam emitted from the light source 40 and that emitted from the light source 41 at the detection area AR) is smaller than about 4/5 of the width L5 of each of the two regions ARf and ARr (i.e., the width of each of the two light beams reaching the detection area AR after emitted from the light sources 40 and 41, respectively). More preferably, as illustrated in FIG. 4, the overlap width L1 is not more than about 1/2 of the width L5. As will be described later, to accurately detect the insufficiency of a sample at the detection area AR, it is desirable that the overlap width L1 is as small as possible. Thus, the two regions ARf and ARr may be separated from each other so that the overlap width L1 is zero.

As illustrated in FIG. 3, in the sample detector B, the light emitted from the light source 40 enters the aperture 60 while spreading to a width L3 which is larger than the width L2 of the light emitting surface of the light source. This light then passes through the aperture 60 to reach the detection area AR. This holds true for the light emitted from the light source 41. When the two light beams respectively emitted from the light sources 40 and 41 reach the light receiving surface (upper surface) of the light receiving element 5, the two beams partially overlap each other with a suitable width L4.

The second light path defining member 7 is made of e.g. a black resin similar to that of the first light path defining member 6 and positioned between the sensor 2 and the light receiving element 5. The aperture 70 of the second light path defining member 7 allows the light having passed through the detection area AR to pass therethrough toward the light receiving element 5 as it is, but blocks other light (external disturbing light) so as not to reach the light receiving element 5.

The controller 8 is structured by using e.g. a microcomputer. The controller performs processing such as the determination as to whether or not blood is properly supplied to the detection area AR based on the signal outputted from the light receiving element 5, the determination of a hematocrit, and the computation of the glucose concentration of blood by reference to the hematocrit, in addition to the drive control of the light sources 40-43. The details will be described later.

An example of specific operation of the measurement device A provided with the sample detector B as well as the advantages thereof is described below.

First, when the sensor 2 is inserted into the case 1 through the opening 11 and set at a predetermined position, the controller 8 drives the light sources 40 and 41 so that the light sources turn on alternately at a constant cycle. In this state, when blood moving through the capillary 24 in the direction indicated by the arrow N1 reaches the region ARf on the upstream side in the detection area AR, the light from the light source 41 impinges on the blood. As a result, the light transmission amount of the region ARf decreases, whereby the level of the signal outputted from the light receiving element 5 decreases. Thereafter, when the blood reaches the area ARr on the downstream side, the light from the light source 40 also impinges on the blood, whereby the light transmission amount the area ARr decreases. In this case again, the level of the signal outputted from the light receiving element 5 decreases.

Figure 5:
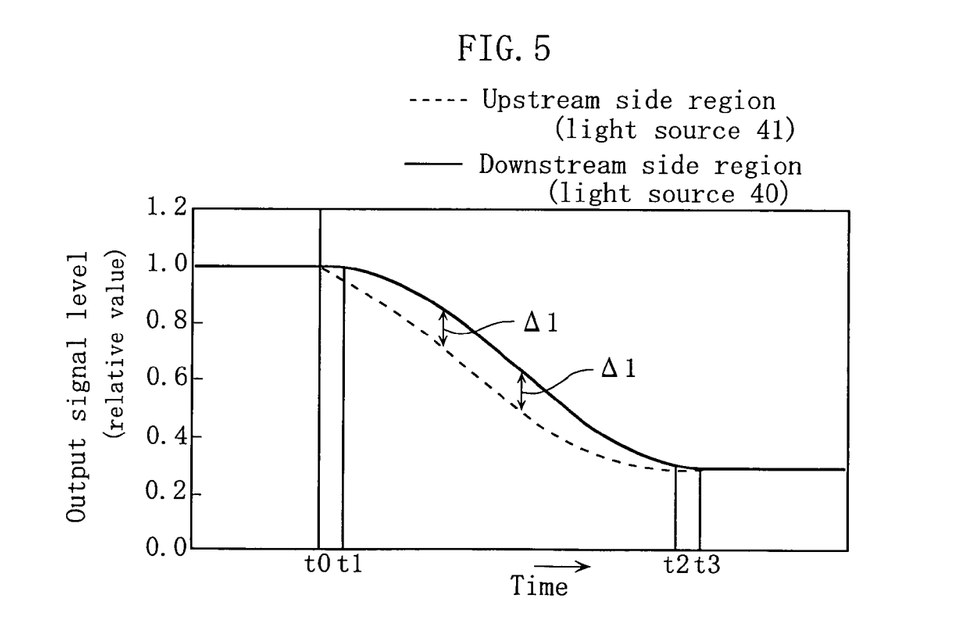
FIG. 5 is an explanatory view illustrating change in level of output signals from a light receiving element in the case where a sample is properly supplied to the detection area illustrated in FIG. 4.

FIG. 5 illustrates the change in level of the output signal from the light receiving element 5 in the above-described process. As illustrated in this figure, the output signal level of the light receiving element 5 when the light source 41 is on (indicated by the broken line in the figure) starts to decrease at the time t0 when the blood comes to the region ARf on the upstream side and stabilizes at a constant level at the time t2. On the other hand, the output signal level of the light receiving element 5 when the light source 40 is on (indicated by the solid line in the figure) starts to decrease at the time t1 which is later than the time t0 and stabilizes at a constant level at the time t3. Thus, when the levels of the two output signals become equal or substantially equal and the difference between the levels is not more than a predetermined threshold at the time t3 and later, it can be determined that blood has sufficiently spread over both of the two regions ARf and ARr. By contrast, as illustrated in FIG. 6, when the levels of the two output signals remain different and the difference Δ2 between the levels is larger than a predetermined threshold still after the time t2, it can be determined that blood has not sufficiently spread to both of the two regions ARf and ARr.

Figure 6:
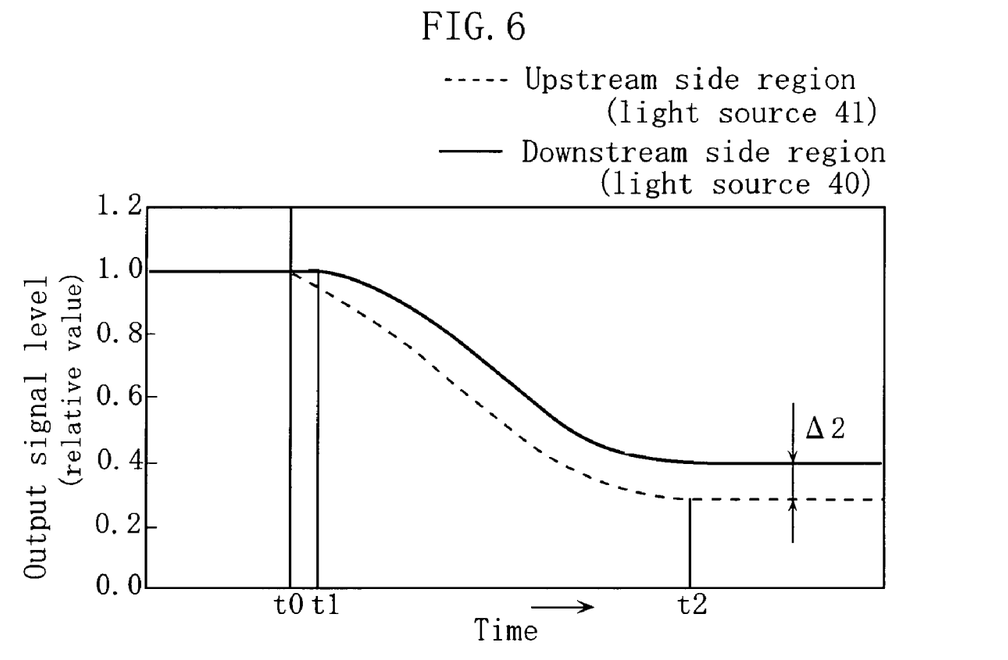
FIG. 6 is an explanatory view illustrating change in level of output signals from the light receiving element in the case where a sample is not properly supplied to the detection area illustrated in FIG. 4.

Preferably, the output signal levels illustrated in FIGS. 5 and 6 are relative values to the output signal level before the time t0 (i.e., the output signal level when blood has not reached the two regions ARf, ARr). Since the relative values precisely correspond to the amount of light absorbed by blood, the use of the relative values is preferable for the accurate determination as to whether or not blood is properly supplied to the detection area AR.

In the sample detector B, the aperture 60 is used to guide the light emitted from the light sources 40 and 41 precisely to the two regions ARf and ARr. This structure achieves lower component cost, easier installation of the component and smaller installation spate than the use of an optical lens to define a light path, for example. Particularly, since a single aperture 60 is used in common for the two light sources 40 and 41, the structure is simple. Thus, the sample detector B can be manufactured at a low cost and made compact.

Figures 7, 7A:
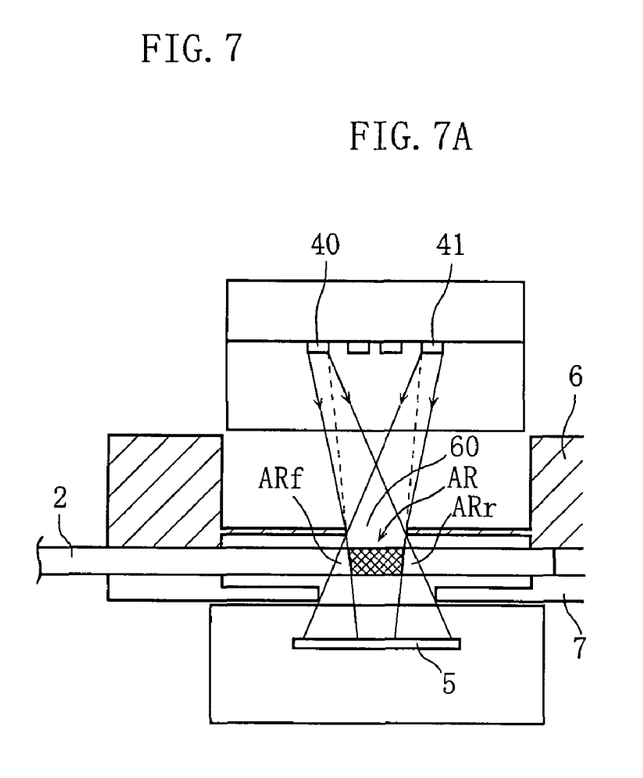
Figure 7B:
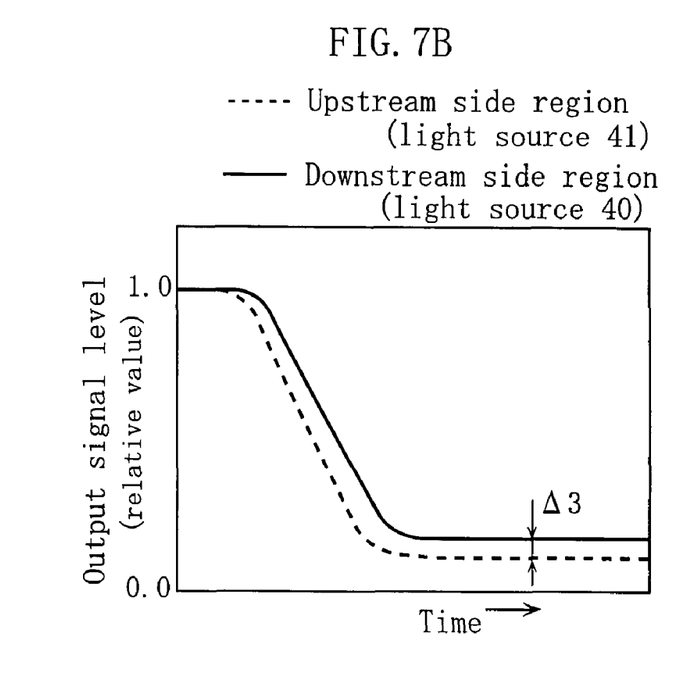
FIG. 7B is an explanatory view illustrating an example of signal outputted from a light receiving element in the comparative example.
Figures 8, 8A:
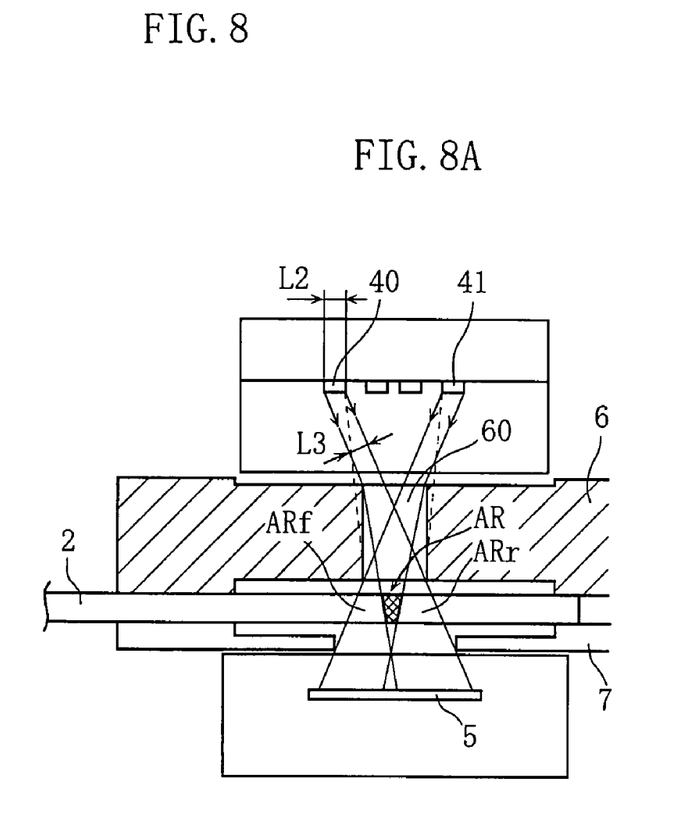

Moreover, in the sample detector B, as described with reference to FIG. 4, the overlap width L1 of the two regions ARf and ARr is not more than about ½ of the width L5, and the area of the portions which do not overlap is large. With this arrangement, when blood is not sufficiently supplied to one of the two regions ARf and ARr, the value Δ2 shown in FIG. 6 is large. FIG. 7A illustrates a comparative example. (This comparative example is also included in the technical scope of the present invention, and this holds true for the comparative example illustrated in FIG. 8A, which will be described later.) In the comparative example illustrated in FIG. 7A, the overlap width of the two regions ARf and ARr (i.e., the width of the portion indicated by cross-hatching) is large. Thus, as shown in FIG. 7B, the difference Δ3 between the two output signal levels when the amount of blood is insufficient is slightly small, which makes it difficult to detect the insufficiency of blood. In the present embodiment, however, such a drawback is eliminated. It is to be noted that, when the overlap width L1 of the two regions ARf and ARr is smaller than about ⅘ of the width L5, the portions of the two regions ARf and ARr which do not overlap each other have enough area. In this case again, therefore, desirable detection performance is provided even when a general-purpose LED is used as the light sources 40, 41 and a general-purpose photodiode is used as the light receiving element 5.

Figure 8B:
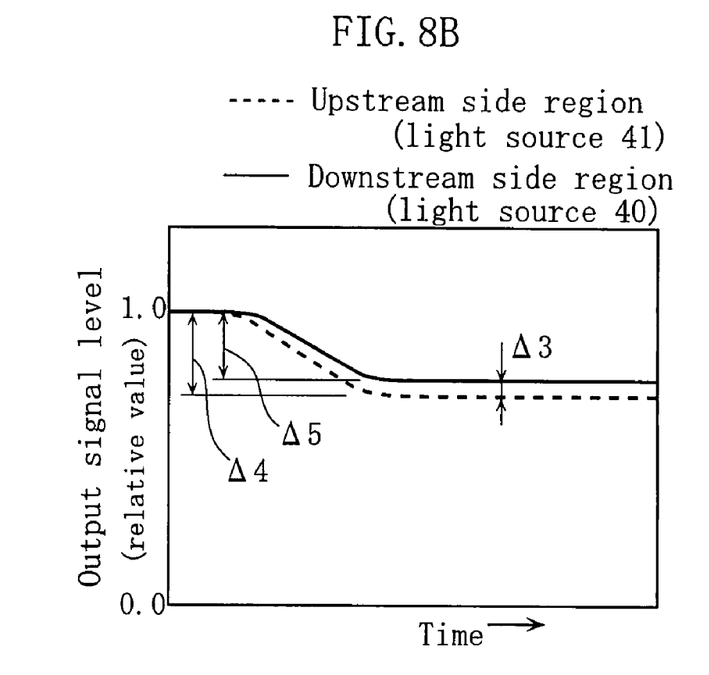
FIG. 8B is an explanatory view illustrating an example of signal outputted from a light receiving element in the comparative example.

As described with reference to FIG. 3, the light emitted from the light sources 40 and 41 to pass through the aperture 60 enters the aperture 60 while spreading to the width L3 which is larger than the width L2 of the light emitting surface. Thus, a sufficient amount of light to irradiate the detection area AR is secured. In the comparative example illustrated in FIG. 8A, although the overlap width of the two regions ARf and ARr is made small, the light traveling from the light sources 40 and 41 toward the aperture 60 does not spread substantially. Instead, the light enters the aperture 60 with the width L3 which is substantially equal to the width L2 of the light emitting surface. In this comparative example, the amount of light to irradiate the detection area AR tends to be insufficient. As a result, as illustrated in FIG. 8B, the difference Δ4, Δ5 between the output signal level when blood exists at the detection area AR and the output signal level when blood does not exist at the detection area AR tends to be small. In this case, the difference Δ3 between the two output signal levels, which is observed when blood is insufficient, is also small. The present embodiment can avoid such a drawback.

In this embodiment, the two light beams respectively emitted from the light sources 40 and 41 partially overlap each other on the light receiving element 5. With this arrangement, the area of the light receiving region on the light receiving element 5 is smaller than that in the case where the above-described two light beams do not overlap each other. Thus, with this embodiment, the overall size of the light receiving element 5 can be made small, which is advantageous.

In addition to the determination described above, the controller 8 performs determination of a hematocrit based on the output signal from the light receiving element 5 obtained by driving the light sources 40 and 41. Specifically, when blood flows to the two regions ARf and ARr of the detection area AR by the capillary action of the capillary 24, the blood reaches the regions ARf and ARr with a time difference, which corresponds to the speed of the blood flow. This speed depends on the viscosity of the blood, and the viscosity of the blood depends largely on the amount of blood cells. Thus, the hematocrit can be determined by determining the speed of the blood flow based on the difference between the time when the blood reaches the region ARf and the time when the blood reaches the region ARr. Based on this principle, the controller 8 determines the hematocrit based on the data on the output signals like those shown in FIG. 5.

More specifically, referring to FIG. 5, the time period from the time t0 to the time t1, the time period from the time t2 to the time t3, the time period from the time t0 to the time t2 or the time period from the time t1 to the time t3 depends on the speed of movement of blood. Thus, the hematocrit can be determined based on the values of the time periods and calibration curve data prepared correspondingly to this in advance. The hematocrit can be determined not only by using the above-described parameter of time but also by using a parameter related to this, which may be the difference Δ1 between the levels of two output signals, the integrated value of the difference Δ1 (i.e., the area of the region surrounded by the curves of the two output signals in FIG. 5) or the rate of change of the light absorptance (i.e., the slope of the curves of the two output signals in FIG. 5).

The above-described determination of a hematocrit is performed by effectively utilizing the sample detector B. Thus, the measurement device A does not need to be provided with additional equipment for exclusive use for the determination of a hematocrit. Thus, the overall structure of the measurement device A is prevented from becoming large or complicated.

In the measurement device A, when blood is supplied to the detection area AR, the glucose concentration of the blood is measured. This processing can be performed by conventionally known techniques. For instance, the detection area AR is irradiated with light from the light sources 42 and 43, and the controller 8 determines the glucose concentration based on the level of a signal outputted from the light receiving element 5 upon the irradiation. The detection area AR develops a color correspondingly to the glucose concentration, and the amount of light absorption by the detection area AR corresponds to the glucose concentration. Thus, the glucose concentration can be determined based on the output signal from the light receiving elements. Preferably, however, instead of obtaining the glucose concentration directly from the output signal from the light receiving element 5, the output signal is corrected to a signal of a level relative to an output signal as a reference obtained when blood is not supplied to the detection area AR, and the glucose concentration is determined based on the corrected signal. The glucose concentration is obtained by checking the level of the signal against the calibration curve data prepared correspondingly to this in advance. As noted before, the measurement device A can obtain a hematocrit. Thus, by correcting the obtained glucose concentration based on the hematocrit, the measurement accuracy is enhanced. The correction of the glucose concentration can be performed by the controller 8 by storing data indicating the relationship between hematocrit values and glucose concentrations in the controller 8 in advance.

In measuring the glucose concentration, the apertures 60 and 70 serve to define the path of the light emitted from the light sources 42 and 43. Thus, it is not necessary to provide another aperture for the light sources 42 and 43, so that the structure of the light path defining members 6 and 7 is simplified. Moreover, in measuring the glucose concentration, the second light path defining member 7 properly prevents the light having passed through portions other than the detection area AR from traveling toward the light receiving element 5. Since the measurement device A includes the sample detector B, when the sample detector B detects that blood is not properly supplied to the detection area AR, the measurement device A can cause the display 12 to display a notice to that effect and cease from performing the measurement of the glucose concentration. Instead of this, when the measurement of the glucose concentration has already been performed, the measurement device can cause the display 12 to display a notice indicating that the measurement is probably incorrect to draw the user's attention.

The present invention is not limited to the foregoing embodiment. The specific structure of each part of the sample detector and the measurement device according to the present invention can be varied in design in various ways.

The opening area or shape of the apertures is not limitative. Two apertures may be provided to correspond to each of the paired light sources. It is only necessary that the aperture is capable of defining the light path of the light emitted from a predetermined pair of light sources and causing the light to travel toward two positionally deviated regions of the detection area. The sample detector of the present invention is suitable for the detection of a blood sample. However, the kind of samples is not limited to this, and samples other than blood can be employed as the detection object. Light sources other than LEDs may also be employed. Any kind of light receiving element can be employed as long as it outputs a signal of a level corresponding to the amount of light received. The measurement device of the present invention can be structured as a device for measuring the concentration of other components such as cholesterol or lactic acid instead of or in addition to glucose concentration.

The invention claimed is:

1. A sample detector comprising:
    at least a pair of light sources for irradiating a detection area as a destination of sample supply with light; and
    a light receiving element which receives two light beams directed from the paired light sources to the detection area and having passed through the detection area and outputs a signal corresponding to the amount of light received; wherein:
    the sample detector further comprises a member provided with at least one aperture positioned between the paired light sources and the detection area; and
    the two light beams emitted from the paired light sources travel through paths defined by the aperture to regions in the detection area which are positionally deviated from each other.

2. The sample detector according to claim 1, wherein the aperture is positioned between the paired light sources in a direction in which the paired light sources are aligned so that both of the two light beams emitted from the paired light sources enter the aperture, and the paths of the two light beams are defined by one aperture.

3. The sample detector according to claim 1, further comprising a determination means, wherein;
    when the paired light sources are individually turned on with a time difference, if levels of two signals outputted from the light receiving element are within a predetermined range and difference between the levels is not more than a predetermined threshold, the determination means determines that a sample is properly supplied to the detection area, and if not so, the determination means determines that a sample is not properly supplied to the detection area.

4. The sample detector according to claim 3, wherein: the determination means sets, as a reference signal, a signal outputted from the light receiving element when the paired light sources are individually turned on in a state in which the sample is not supplied to the detection area; and
    in determining whether or not a sample is supplied to the detection area, the determination means corrects a signal outputted from the light receiving element to a signal having a relative value to the reference signal and makes determination based on the corrected signal.

5. The sample detector according to claim 1, wherein the two light beams emitted from the paired light sources do not overlap each other in the detection area or overlap each other with an overlap width which is smaller than about $4/5$ of width of each of the light beams.

6. The sample detector according to claim 1, wherein light which has entered the aperture while spreading from a light emitting surface of each of the light sources to a width larger than width of the light emitting surface passes through the aperture to reach the detection area.

7. The sample detector according to claim 1, wherein the two light beams emitted from the paired light sources partially overlap each other on the light receiving element.

8. The sample detector according to claim 1, wherein a member provided with an additional aperture for allowing light having passed through the detection area to travel toward the light receiving member is arranged between the detection area and the light receiving element so that external disturbing light which has not passed through the detection area is prevented from traveling toward the light receiving element.

9. A measurement device comprising:
    a sample detector which sets a destination of sample supply as a detection area; and
    a measurement means capable of performing predetermined measurement with respect to a sample supplied to the detection area;
    the sample detector comprising:
        at least a pair of light sources for irradiating the detection area with light;
        a light receiving element which receives two light beams directed from the paired light sources to the detection area and having passed through the detection area and outputs a signal corresponding to the amount of light received; and
        a member provided with at least one aperture positioned between the paired light sources and the detection area;
        wherein the two light beams emitted from the paired light sources travel through paths defined by the aperture to regions of the detection area which are positionally deviated from each other.

10. The measurement device according to claim 9, wherein: the measurement means is capable of measuring concentration of a particular component in a blood sample; and
    when a blood sample is caused to flow successively to each of the two positionally deviated regions of the detection area from one side thereof, speed of the flow of the blood sample is determined based on an output signal from the light receiving element which is obtained by directing light from the two light sources to the two regions, and information about hematocrit of the blood sample is obtained.

11. The measurement device according to claim 10, wherein: the measurement means includes at least one additional light source; and
    light emitted from the additional light source is received by the light receiving element after passing through the aperture and traveling to the detection area, and information about concentration of a particular component in the blood sample is obtained based on an output signal from the light receiving element.

* * * * *